US00PP33358P2

(12) United States Plant Patent
Martinez

(10) Patent No.: US PP33,358 P2
(45) Date of Patent: Aug. 17, 2021

(54) SEEDLESS TABLE GRAPE (GRAPEVINE) 'ITUMEIGHTEEN'

(50) Latin Name: *Vitis vinifera*
Varietal Denomination: ITUMEIGHTEEN

(71) Applicant: Investigacion y Tecnologia de Uva de Mesa S.L., Blanca (ES)

(72) Inventor: Manuel Tornel Martinez, La Alberca (ES)

(73) Assignee: Investigacion y Tecnologia de Uva de Mesa S.L.

( * ) Notice: Subject to any disclaimer, the term of this patent is extended or adjusted under 35 U.S.C. 154(b) by 0 days.

(21) Appl. No.: 17/015,623

(22) Filed: Sep. 9, 2020

(51) Int. Cl.
*A01H 5/08* (2018.01)
*A01H 6/88* (2018.01)

(52) U.S. Cl.
USPC ..... Plt./205

(58) Field of Classification Search
USPC ..... Plt./156, 205, 206
See application file for complete search history.

(56) References Cited

PUBLICATIONS

UPOV-PLUTO: plant variety database, Feb. 9, 2021, citation for 'Itumeighteen'. 1 pg. (Year: 2021).*

* cited by examiner

*Primary Examiner* — Susan McCormick Ewoldt
*Assistant Examiner* — Karen M Redden

(57) ABSTRACT

A new and distinct variety of grapevine named of 'ITUMEIGHTEEN' is herein disclosed. 'ITUMEIGHTEEN' forms medium sized bright red colored berries with a unique cylindrical with narrowed mid-section shape, a slightly acidic Muscat flavor and a firm berry texture. Being mid-season variety, the fruit commonly is ready for harvesting in from July to early September in Blanca, Murcia, Spain. 'ITUMEIGHTEEN' displays good eating qualities as a table grape, the fruit meatiness and firmness render the fruit amenable for handling, shipping, and storage.

5 Drawing Sheets

Latin name of the genus and species: *Vitis vinifera.*
Variety denomination: 'ITUMEIGHTEEN'.

BACKGROUND OF THE INVENTION

A breeding program was initiated during 2003 at a research nursery in Blanca, Murcia, Spain. During the development of this breeding program, a new variety of *Vitis vinifera* was created by deliberate cross breeding of two parent plants by emasculation of the pollen bearing organ of the female and introducing pollen from another male origin. The female parent of the new variety is 'IT02-12-15', an unpatented proprietary selection. The male parent (i.e. the pollen parent) of the new variety is 'Princess', unpatented.

'ITUMEIGHTEEN' was identified as a potentially interesting selection during 2010 at the same location in Murcia, Spain. After identifying the new variety as a potentially interesting selection, first propagation of 'ITUMEIGHTEEN' by vegetative cuttings was undertaken during 2011, at the research nursery in Murcia, Spain. Controlled testing and propagation of the new variety continued, to assess stability of the unique characteristics of this variety. Subsequently, several generations have been reproduced and have shown that the unique features of this cultivar are stable and reproduced true to type. No commercial sales occurred before the filing of the US plant patent application.

SUMMARY OF THE INVENTION

The cultivar 'ITUMEIGHTEEN' has not been observed under all possible environmental conditions. The phenotype may vary somewhat with variations in environment such as temperature, day length, and light intensity, without, however, any variance in genotype. The new variety 'ITUMEIGHTEEN' is pink seedless table grape with medium production and a high fertility index "1, 6". In addition to the before mentioned characteristics, the following traits have been repeatedly observed and are determined to be the unique characteristics of 'ITUMEIGHTEEN' These characteristics in combination distinguish 'ITUMEIGHTEEN' as a new and distinct *Vitis* cultivar:

1. Medium sized individual fruit with bright red skin coloration; formed in medium-to-large clusters.
2. Unique individual berry shape: cylindrical, with a narrowed mid-section, somewhat hourglass shaped.
3. A mid-season season variety, commonly bears fruit for harvesting from July until early September in the region of Murcia, Spain.
4. Very crunchy berry texture.
5. Seedless.
6. Resistance to cracking.
7. Fruit has been found to be suitable for handling and shipping.
8. Observed tolerance of water shortage.
9. Observed tolerance for temperatures up to 41° C.
10. Interesting lightly acidic muscat flavor profile.

COMPARISON TO PARENT VARIETIES

TABLE 1

| Characteristic | 'ITUMEIGHTEEN' | Parental A (fem) 'IT02-12-15' |
|---|---|---|
| Berry flavor | Lightly acidic muscat | Neutral |
| Formation of Seeds | Seedless | Lignified |
| Fertility Index | 1 | 1.3 |

| Characteristic | 'ITUMEIGHTEEN' | Parental B (masc.) 'Princess' |
|---|---|---|
| Berry Flavor: | Lightly acidic muscat | Muscat |
| Berry Skin Color | Red | Yellow |
| Berry Shape: | Cylindrical with narrowed mid-section | Ovoid |

COMMERCIAL COMPARISON

TABLE 2

| Characteristic | 'ITUMEIGHTEEN' | 'Flame' (unpatented) |
|---|---|---|
| Berry Shape | Cylindrical with narrowed mid-section | Globose |
| Berry flavor | Lightly acidic muscat | Very sweet |

| Characteristic | 'ITUMEIGHTEEN' | 'Crimson' (unpatented) |
|---|---|---|
| Berry Shape | Cylindrical with narrowed mid-section | Elongated ellipsoid |
| Berry Flavor | Muscat | Neutral |

BRIEF DESCRIPTION OF THE PHOTOGRAPHS

The accompanying photographic illustrations show typical samples of vegetative growth of a 5 year old specimen of the new variety, in color as nearly true as it is reasonably possible to make in a color illustration of this character. Plants were grown in Murcia, Spain. Colors in the photograph may differ from the color values cited in the detailed botanical description below, which accurately describes the colors of the new Grapevine.

DETAILED BOTANICAL DESCRIPTION

Figure 1:
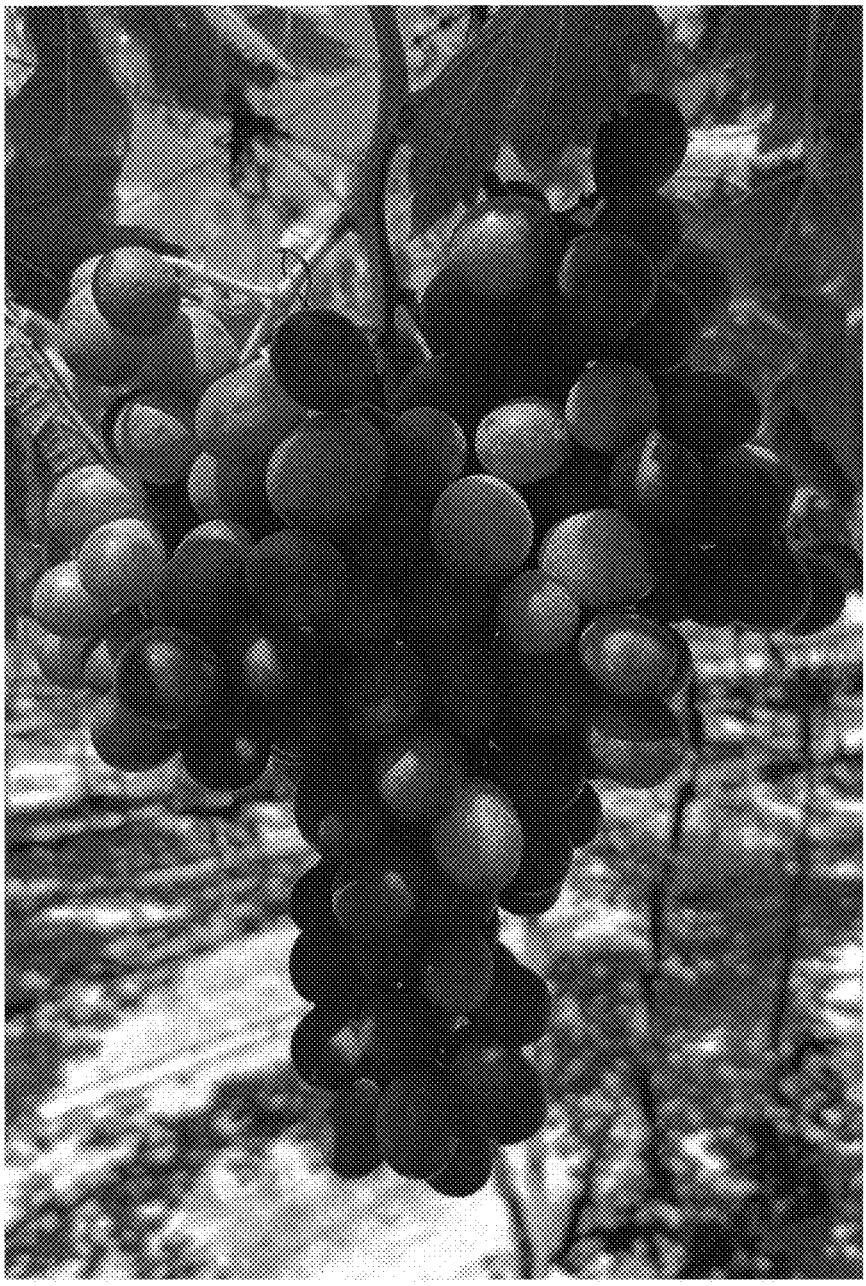
FIG. 1 illustrates a fruit cluster of 'ITUMEIGHTEEN'.
Figure 2:
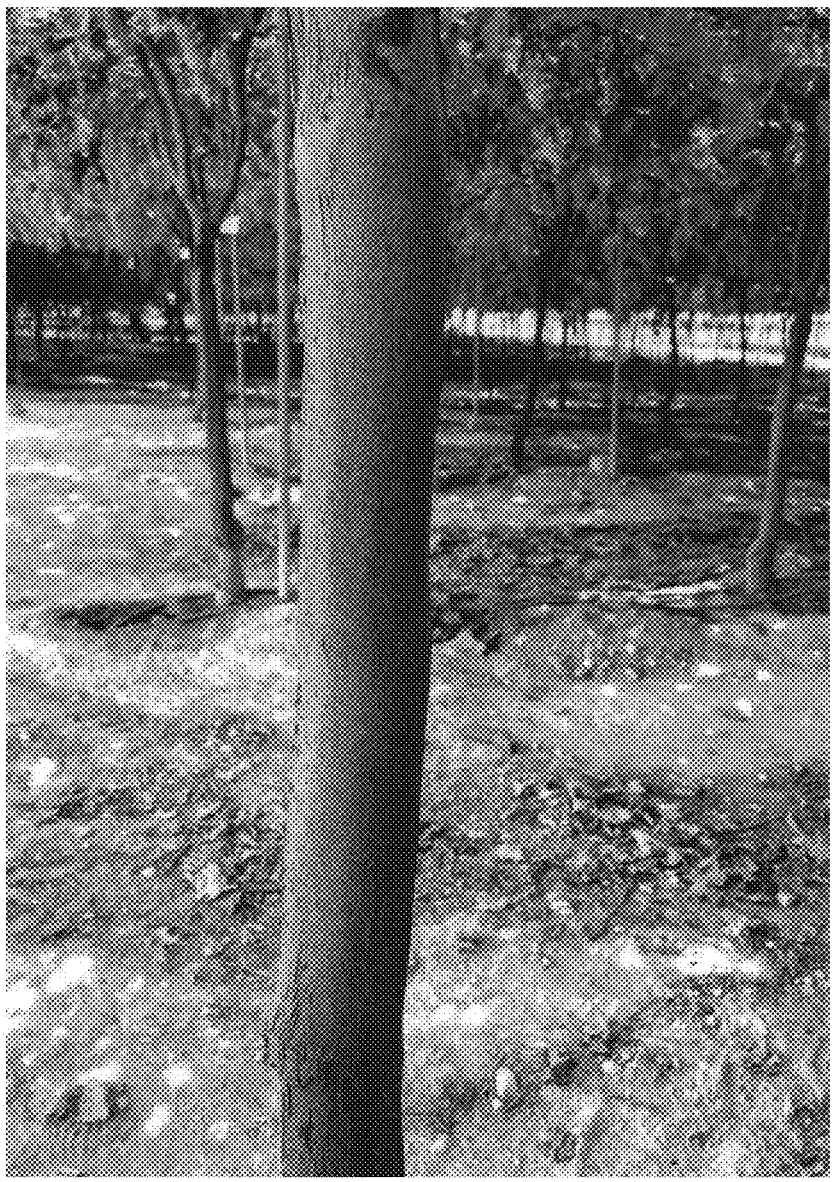
FIG. 2 shows a close-up view of the trunk of 'ITUMEIGHTEEN'.
Figure 3:
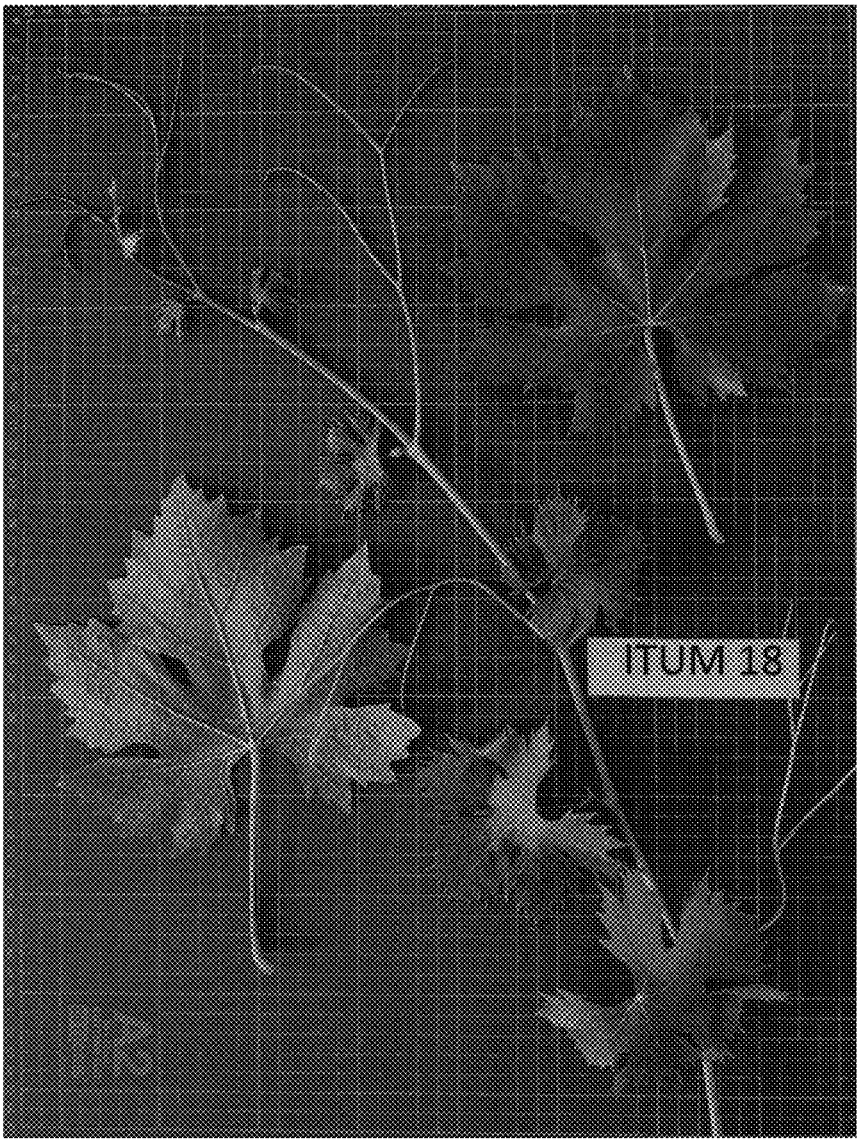
FIG. 3 illustrates in close up perspective typical foliage of the new variety, both front and back of the leaf, as well as immature foliage.
Figure 4:
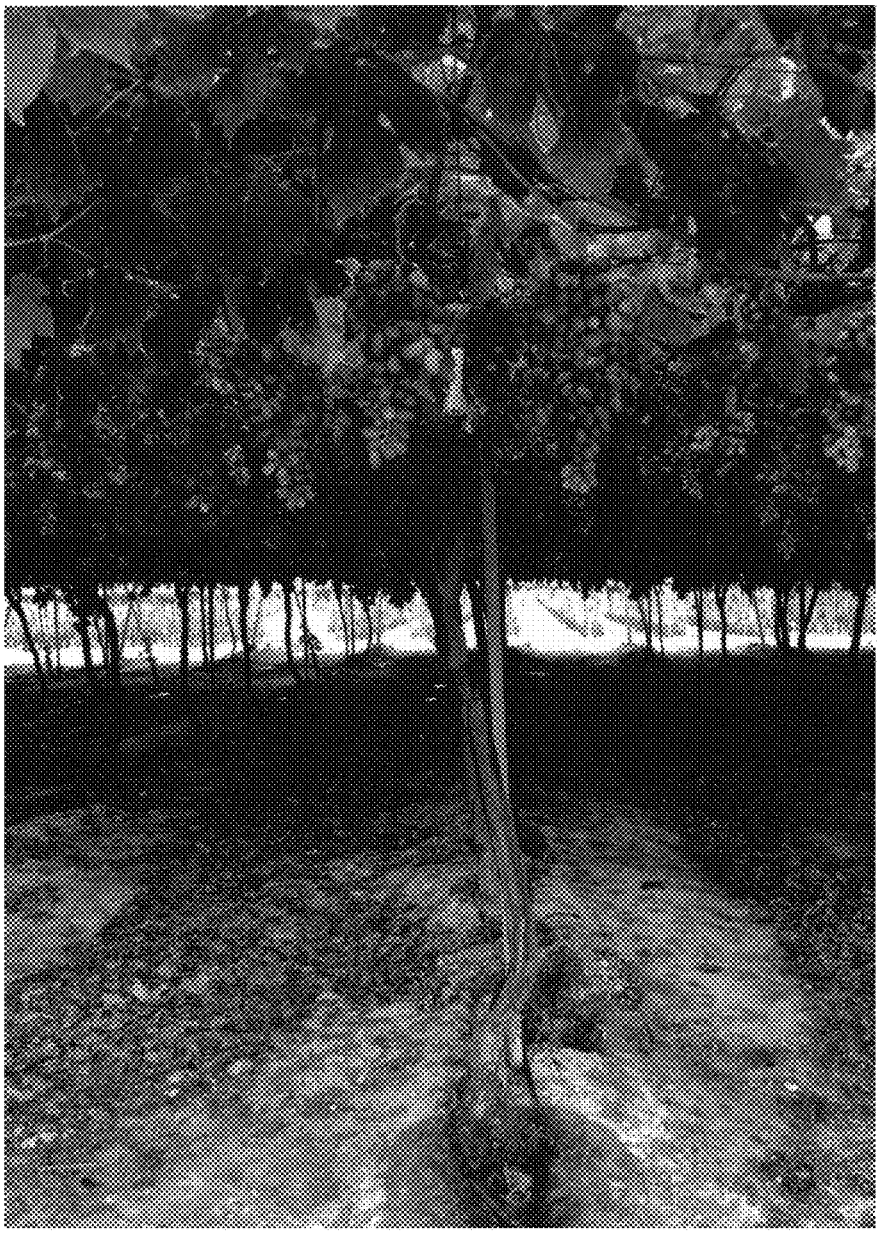
FIG. 4 illustrates a small test field of fruiting vines of the new variety.
Figure 5:
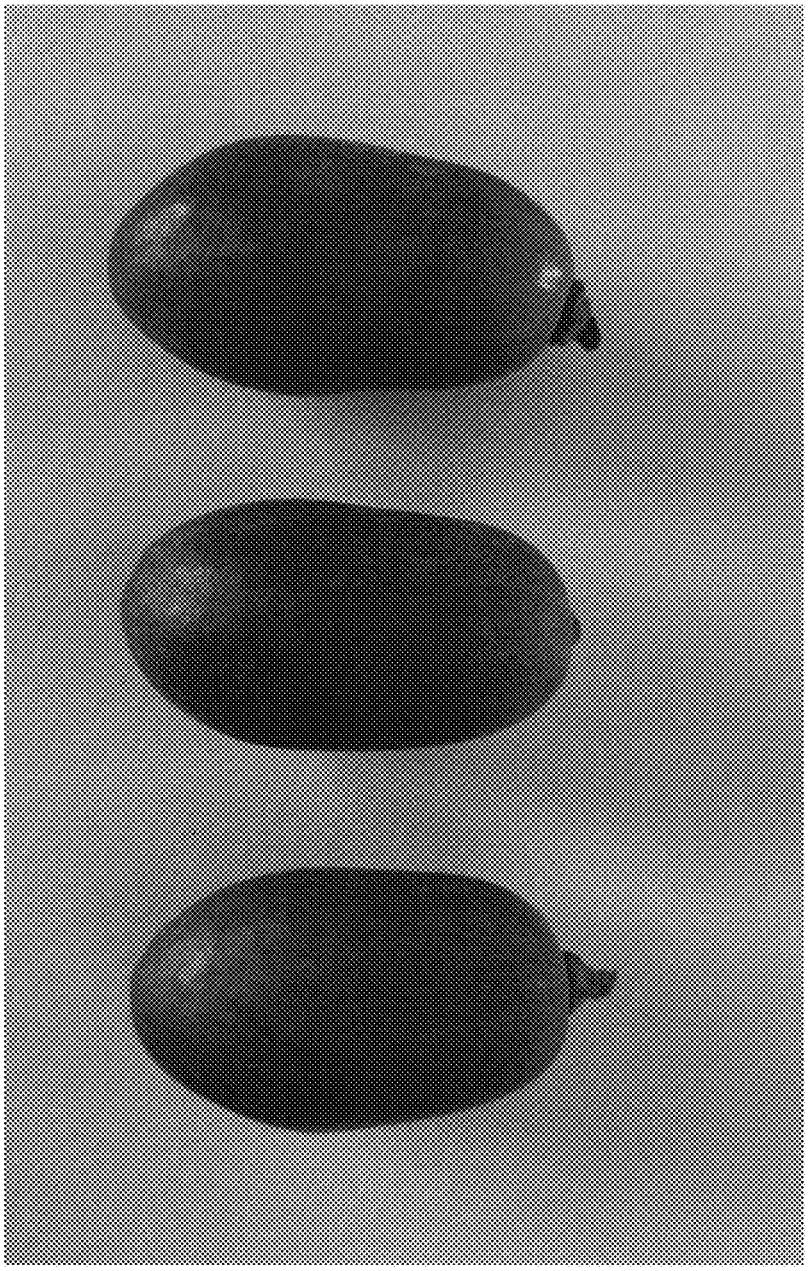
FIG. 5 illustrates individual berries of the new variety.

In the following description, color references are made to The Royal Horticultural Society Colour Chart 2015 except where general terms of ordinary dictionary significance are used. Some descriptors, when useful have been incorporated from *UPOV Grape Descriptor Guidelines*. The description is based on the observation of plants growing on '1103 Paulsen' (not patented) rootstock in clay stony soil conditions in the fields near Blanca, Murcia, Spain. The age of plant described is of 5 years, with an average height of 200 cm, a high canopy density, a 300 cm plant spread, a one-year growth rate to reach two meters high and 20 to 30 days to initiate roots at approx. 20° C. At observation location temperature ranged between 15° C. to 35° C. during the day, and between 5° C. to 20° C. during the night.

Botanical classification: *Vitis vinifera* 'ITUMEIGHTEEN'.

CANES

Characteristics of mature canes:

*Diameter.*—1.5 to 3.0 cm.
*Length.*—60 to 90 cm.
*Color.*—Medium light brown (164C RHS).
*Cross section shape.*—Circle.
*Strength.*—Medium.
*Texture.*—Non-pubescent, rough.

Lenticels: Diameter <0.5 mm.

*Density.*—Few to-moderate.
*Color.*—Medium light brown (164C RHS).

Internode length: 9-12 cm; midpoint 10 cm.

*Pigmentation at internode, dorsal.*—Near RHS Greyed-Orange 164C).
*Pigmentation at internode, ventral.*—Near RHS Greyed-Orange 164C).

Tendril pattern on show: 0, 0, 0,0,1,0 or 0,0,0,0 0, 1.

*Tendrils forked.*—Yes.
*Tendril texture.*—Glabrous.
*Tendril length.*—6 to 11 cm.

Bud:

*Bud width.*—1.5 cm.
*Bud length.*—0.3 cm.
*Bud shape.*—Flattened.
*Bud color.*—Light yellow brown Near RHS Greyed-Yellow 161A, flushed 162B.

Young shoot:

*Openness of tip.*—Open. Anthocyanin not present in Shoot pigmentation.
*Texture.*—Smooth.
*Diameter.*—0.8 to 1.1 cm.
*Longitudinal length.*—1.0 to 4.0 m; average 1.2 m.
*Color.*—Near RHS Greyed-Orange 164D, streaked 165D.
*Cross section.*—Circular.
*Strength.*—Medium.
*Attitude.*—Horizontal.
*Bark texture.*—Shaggy.
*Bark color.*—Near RHS Greyed-Red 179A streaked 180B.

FOLIAGE

Leaf:

*Arrangement.*—Alternate.
*Quantity.*—Approximately 16 per cane.
*Average length.*—17.5 cm.
*Average width.*—19.5 cm.
*Overall shape of blade.*—Orbicular.
*Lobes.*—5 lobes.
*Apex.*—Acute.
*Base.*—Rounded.

*Margin*.—Dentate. Dentations about 1 mm to 15 mm. Ratio of length to width about 1.2 to 1. Mature teeth a mixture of both sides straight and both sides slightly convex.
*Texture of top surface*.—Smooth.
*Texture of bottom surface*.—Smooth.
*Pubescence*.—None.
*Aspect*.—Undulate.

Sinuses:
*Shape of petiolar sinus*.—Deep widened.
*Shape of base petiolar sinus*.—Deep widened.
*Depth of petiolar sinus*.—2.8 cm.
*Width of petiolar sinus*.—2.2 cm.
*Shape of upper sinuses*.—Shallow widened, slightly overlapping.

Color:
*Immature foliage upper side*.—Near RHS Yellow-Green 154D streaked 150D.
*Immature foliage under side*.—Near RHS Yellow-Green 154D streaked 150D.
*Mature foliage upper side*.—Near RHS Green 137A.
*Mature foliage under side*.—Near RHS Yellow-Green 144A.

Venation: Type: pinnate.
*Venation color upper side*.—Near RHS Yellow-Green 154C.
*Venation color under side*.—Near RHS Yellow-Green 154C.
*Anthocyanin coloration*.—Not present.

Petiole:
*Length*.—12.5 cm.
*Diameter*.—0.3 cm.
*Color*.—Near RHS Yellow-Green 144A with weak Anthocyanin presence near base, Red 36C.
*Texture*.—Moderately rough.

FLOWER

Flowering period begins around May 1 to 5 in Murcia, Spain.

Inflorescence when in bud:
*Length*.—8 cm.
*Diameter*.—3 cm.
*Bud color*.—Near RHS Green 140B.
*Bud shape*.—Conical.
*Bud size*.—About 1 to 2 mm by 1 to 2 mm.

Individual flower:
*Main time of flowering*.—9 days.
*Size of entire flower* (*to end of stamens*).—0.7 cm.
*Calyx shape*.—Funnel.
*Calyx size*.—12 mm.
*Calyx color*.—Near RHS Green 140B.
*Calyx apex*.—Rounded.
*Calyx base*.—Rounded.
*Calyx texture*.—Glabrous all surfaces.
*Diameter*.—7 mm.
*Quantity per flowering stem*.—5.
*Days lasting on plant*.—9 days.

Petals:
*Quantity*.—5.
*Arrangement*.—Symmetrical rotate.
*Length*.—0.17 cm.
*Width*.—<0.1 cm.
*Shape*.—Obovate.
*Apex*.—Ovate.
*Base*.—Ovate.
*Texture, upper and lower surfaces soft*.—
*Color*.—At opening upper surface: Near RHS Green 140B. At opening lower surface: Near RHS Green 140B. Fully opened upper Surface: Near RHS Green 140B.

Peduncles:
*Fruit peduncle length*.—60 mm.
*Fruit peduncle width*.—3.5 mm.
*Angle*.—About 60° to the lateral branch.
*Fruit peduncle strength*.—Firm-hard.
*Fruit peduncle texture*.—Soft.
*Color*.—Light green (142D RHS).

Pedicels:
*Length*.—0.4 cm.
*Diameter*.—0.1 cm.
*Angle*.—About 80° to center of flower cluster.
*Strength*.—Medium.
*Texture*.—Softly pubescent.
*Color*.—Near RHS Green 141C.

Fragrance: Absent.

REPRODUCTIVE ORGANS

Number of stamens: 5.

Anthers:
*Shape*.—Oblong.
*Length*.—Approximately 0.05 cm.
*Color*.—Near Yellow 10A.

Pollen: Color: Near Yellow 8A.
Quantity: Abundant.
Pistil quantity: 1.
*Length*.—0.25 cm.
Style: Length: <0.1 cm.
*Color*.—Near RHS Green 143B.
Stigma: Shape: round.
*Color*.—Near RHS Yellow-Green 144C.
Ovary color: Near RHS Yellow-Green 144D.

FRUIT

Cluster:
*Average length*.—20 cm.
*Average diameter*.—18 cm.
*Average weight*.—550 grams.
*Fertility index*.—number of clusters per sprouted buds 1.

Fruit:
*Average length*.—2.8 cm.
*Average diameter*.—2.2 cm.
*Shape*.—Cylindrical with narrowed mid-section.
*Cross-section*.—circular.
*Color of berry skin*.—Near RHS Red 44A and Red 43A.
*Color of berry flesh*.—Translucent, near White 155B, with slight to moderate anthocyanin near Greyed-Red 180D.
*Brix at harvest*.—20.
*Ease of detachment from pedicle*.—Difficult, well hooked and difficult detachment.
*Thickness of skin*.—Thin.
*Firmness of flesh*.—Very crunchy and firm.
*Particular flavor*.—Lightly acidic muscat.
*Fruit peduncle length*.—75 mm.
*Fruit peduncle width*.—5 mm.
*Fruit peduncle texture*.—Firm, hard.

*Fruit peduncle color*.—Near Green 142D.
*Formation of seeds*.—Not present.
*Time of beginning of berry ripening*.—Early July in Murcia, Spain.
*Productivity*.—Approximately 40,000 kilos per hectare.

OTHER CHARACTERISTICS

Disease and pest resistance: Not observed to be susceptible nor resistant to normal diseases and pests of *Vitis vinifera*.

Temperature tolerance: Observed growing between 6° C. to 41° C.

Temperature tolerance: Observed to tolerate water shortages during the dry Summer months of Murcia, Spain without detriment.

What is claimed is:

1. A new and distinct cultivar of *Vitis* grapevine named 'ITUMEIGHTEEN' as herein illustrated and described.

* * * * *